United States Patent [19]

Bright

[11] Patent Number: 4,464,527

[45] Date of Patent: Aug. 7, 1984

[54] ANTIBACTERIAL 9-DEOXO-9A-ALKYL-9A-AZA-9A-HOMO-ERYTHROMYCIN A DERIVATIVES AND INTERMEDIATES THEREFORE

[75] Inventor: Gene M. Bright, Groton, Conn.

[73] Assignee: Pfizer Inc., New York, N.Y.

[21] Appl. No.: 509,538

[22] Filed: Jun. 30, 1983

[51] Int. Cl.³ .............................................. C07H 17/08
[52] U.S. Cl. ..................................... 536/7.4; 424/180; 536/7.2
[58] Field of Search ................... 536/7.2, 7.4; 424/180

[56] References Cited

U.S. PATENT DOCUMENTS 4,328,334  5/1982  Kobrehel et al. .................... 536/7.4

FOREIGN PATENT DOCUMENTS 892357  7/1982  Belgium ............................... 536/7.4
2094293  9/1982  United Kingdom ................. 536/7.4

OTHER PUBLICATIONS

U.S. patent appln. Ser. No. 441,981; filed Nov. 15, 1982; Group Art Unit 125; applicant Gene M. Bright; Summary of the Invention, pp. 2–5.

*Primary Examiner*—Johnnie R. Brown
*Attorney, Agent, or Firm*—Charles J. Knuth; Albert E. Frost; James M. McManus

[57] ABSTRACT

Antibacterial 9-deoxo-9a-ethyl and propyl-9a-aza-9a-homoerythromycin A compounds, pharmaceutically acceptable salts thereof, pharmaceutical compositions comprising antibacterially effective amounts thereof and a pharmaceutically acceptable carrier, the treatment of bacterial infections with antibacterially effective amounts thereof, and intermediates and processes for their preparation.

5 Claims, No Drawings

ANTIBACTERIAL 9-DEOXO-9A-ALKYL-9A-AZA-9A-HOMOERYTHROMYCIN A DERIVATIVES AND INTERMEDIATES THEREFORE

BACKGROUND OF THE INVENTION

This invention relates to novel derivatives of 9-deoxo-9a-aza-9a-homoerythromycin A, to intermediates therefor and to processes for their preparation. More particularly it relates to 9a-ethyl and 9a-n-propyl derivatives of 9-deoxo-9-a-aza-9a-homoerythromycin A, to pharmaceutically acceptable acid addition salts thereof and the use of said compounds as antibacterial agents, to intermediates therefor, and to processes for their preparation.

Erythromycin A is a macrolide antibiotic produced by fermentation and described in U.S. Pat. No. 2,653,899. Numerous derivatives of erythromycin A have been prepared in efforts to modify its biological and/or pharmacodynamic properties. Erythromycin A esters with mono- and dicarboxylic acids are reported in Antibiotics Annual, 1953–1954, Proc. Symposium Antibiotics (Washington, D.C.), pages 500–513 and 514–521, respectively. U.S. Pat. No. 3,417,077 describes the cyclic carbonate ester of erythromycin A, the reaction product of erythromycin A and ethylene carbonate, as an active antibacterial agent.

U.S. Pat. No. 4,328,334, issued May 4, 1982 describes 9-deoxo-9a-aza-9a-homoerythromycin A and refers to it by the name 11-aza-10-deoxo-10-dihydroerythromycin A. Since said compound is a ring expanded (homo) derivative of erythromycin A, nitrogen (aza) being the additional atom of the ring system, the nomenclature 9-deoxo-9a-aza-9a-homoerythromycin A is preferred for the parent ring system of the compounds of this invention.

Belgian Pat. No. 892,357, published July 1, 1982, and its British counterpart, Application No. 2,094,293A, published Sept. 15, 1982, disclose the N-methyl derivative of 9-deoxo-9a-aza-9a-homoerythromycin A, as does my co-pending U.S. application Ser. No. 441,981, filed Nov. 15, 1982, which claims priority from U.S. application Ser. No. 399,401, filed July 19, 1982, now abandoned. The 4"-epimer of said N-methyl derivative is the subject of my co-pending U.S. application Ser. No. 441,979, filed Nov. 15, 1982. My co-pending U.S. application Ser. No. 497,473 filed May 23, 1983 and now abandoned, claims cyclic ether derivatives of 9-deoxo-9a-aza-9a-homoerythromycin A and its 4"-epimer.

U.S. Pat. No. 4,382,085, issued May 3, 1983 describes 4"-epi erythromycin A; i.e., the 4"—OH group has the axial configuration. The 4"—OH in erythromycin A has the equatorial configuration.

SUMMARY OF THE INVENTION

It has now been found that 9a-ethyl and 9a-n-propyl derivatives of 9-deoxo-9a-aza-9a-homoerythromycin A are effective antibacterial agents against Gram-positive and Gram-negative bacteria. The compounds have the formula (I)

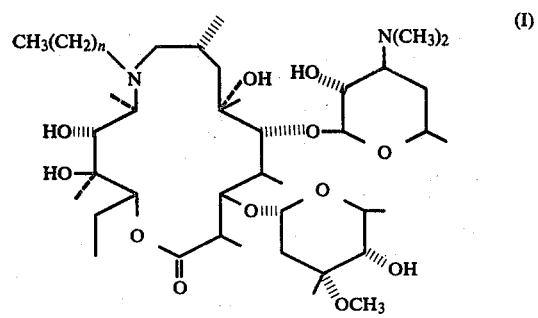

wherein n is 1 or 2.

Also included in this invention, and useful for the same purpose as formula (I) compounds, are the pharmaceutically acceptable acid addition salts thereof. Included among said salts, but by no means limited to said salts, are those enumerated below: hydrochloride, hydrobromide, sulfate, phosphate, formate, acetate, propionate, butyrate, citrate, glycolate, lactate, tartrate, malate, maleate, fumarate, gluconate, stearate, mandelate, pamoate, benzoate, succinate, lactate, p-toluenesulfonate and asparate.

The present invention also embraces processes and intermediates useful for the preparation of compounds of formula (I). The intermediates are represented by formula (II) below:

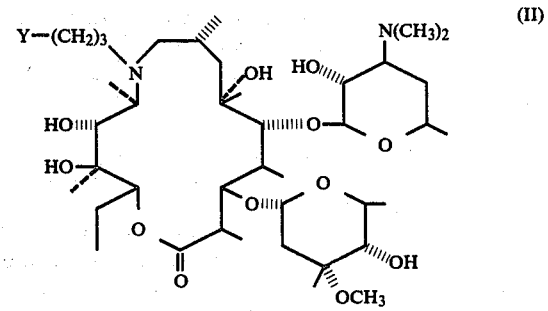

wherein Y is —NHCHO or

The first process for preparing a compound of formula (I) wherein n is 2 comprises reacting a compound of formula (II) wherein Y is

with tri-n-butyl tin hydride and azobisisobutylnitrile in a reaction-inert solvent at a reaction temperature of about 125° C. The preferred solvent is xylene.

The other process of this invention leading to a compound of formula (I) wherein n is 1 comprises reacting a compound of the formula

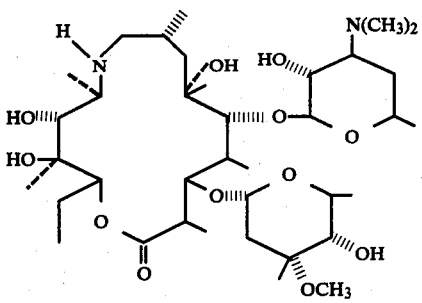

with (a) aqueous acetaldehyde in the presence of hydrogen and palladium-on-charcoal in a reaction-inert solvent, wherein the preferred solvent is ethanol, or alternately, (b) acetaldehyde and sodium cyanoborohydride in a reaction-inert solvent at a pH of about 5.9, wherein the preferred solvent is methanol.

Also within the scope of the present invention is a pharmaceutical composition comprising an antibacterial amount of a compound of formula (I) and a pharmaceutical carrier, and a method for treating a bacterial infection in a mammal which comprises administering to said mammal an antibacterial effective amount of a compound of formula (I).

Compounds of formula (I) and pharmaceutically acceptable acid addition salts thereof are effective antibacterial agents against Gram-positive microorganisms, e.g. *Staphylococcus aureus* and *Streptococcus pyogenes*, and against Gram-negative microorganisms, e.g., *Pasturella multocida* and *Neisseria sicca* in vitro. Additionally, compounds of formula (I) exhibit significant activity against *Neisseria gonorrhea* and Haemophilus in vitro and against many Gram-positive and Gram-negative microorganisms in vivo. In their useful oral activity and unexpectedly long serum half-life in mammals, the formula (I) compounds are like 9-deoxo-9a-methyl-9a-aza-9a-homoerythromycin A, and quite unlike the corresponding 9a-desmethyl compound 9-deoxo-9a-aza-9a-homoerythromycin A which exhibits no practical oral activity in vivo, and a substantially shorter serum half-life.

DETAILED DESCRIPTION OF THE INVENTION

The compound of formula (I) wherein n is 1 is prepared by the reductive alkylation of 9-deoxo-9a-aza-9a-homoerythromycin A using aqueous acetaldehyde and hydrogen in the presence of a palladium-on-charcoal catalyst in a reaction-inert solvent.

In practice, the 9-deoxo-9a-aza-9a-homoerythromycin A is combined with at least a ten fold excess of acetaldehyde in a reaction solvent containing about an equal weight of 5% palladium-on-charcoal. The resulting mixture is shaken at room temperature in a hydrogen atmosphere at an initial pressure of about 50 psi. Under these conditions the reaction is usually complete in about twelve to sixteen hours.

On completion of the reaction the catalyst is filtered and the product obtained by conventional means. If a purer product is desired it may be so purified by conventional means such as recrystallization or chromatography.

It is preferable to employ aqueous acetaldehyde, for example, a 37% solution of acetaldehyde in water.

The reaction-inert solvent employed in the aforementioned process should be one which amply solubilizes the reactants and does not react to any appreciable extent with the starting reagents or product. In this particular process the preferred solvent is ethanol although it is appreciated that a large number of other solvents may be employed with similar results.

A second type of reductive alkylation reaction used to prepare a compound of formula (I) wherein n is 1 comprises reacting 9-deoxo-9a-aza-9a-homoerythromycin A with acetaldehyde and sodium cyanoborohydride in a reaction-inert solvent at a pH of about 5.9.

In practice, 9-deoxo-9a-aza-9a-homoerythromycin A is combined with a one hundred fold molar excess of acetaldehyde in an appropriate reaction-inert solvent, and the pH adjusted to about 5.9 with acetic acid. To the resulting mixture is added over a period of about ten minutes a five fold molar amount of sodium cyanoborohydride. If needed the pH is adjusted by the addition of acetic acid.

The preferred reaction-inert solvent, having the aforementioned characteristics for this reaction is methanol, although many other solvents can be used with similar results.

At ambient temperatures the reaction is generally complete in about sixteen to eighteen hours. Shorter reaction times are possible if the reaction temperature is raised above room temperature.

The product is obtained by means familiar to those skilled in the art. Further purification can be achieved by normal methods such as recrystallization or chromatography.

Preparation of a compound of formula (I) wherein n is 2 comprises treating a compound of formula (II) wherein Y is

with tri-n-butyl tin hydride in a reaction-inert solvent.

In practice, 9-deoxo-9a-(gamma-isonitrilopropyl)-9a-aza-9a-homoerythromycin A

is combined with a fifty fold molar amount of tri-n-butyl tin hydride in an appropriate solvent, and the temperature raised to about 125° C. To the hot reaction mixture is added over a period of one hour a five fold molar amount of azobisisobutylnitrile. The reaction temperature is maintained for about forty-five minutes after completion of the addition.

The preferred reaction-inert solvent for the aforedescribed process is xylene, although many other solvents can be employed with similar results.

On completion of the reaction the product is isolated by conventional means and purified by chromatographing on silica gel.

The preparation of the compound of formula (II) wherein Y is

and other necessary intermediates useful for this process are described hereafter in the examples.

Also considered part of the present invention are the 4''-epimers of the compounds of formula (I) as follows:

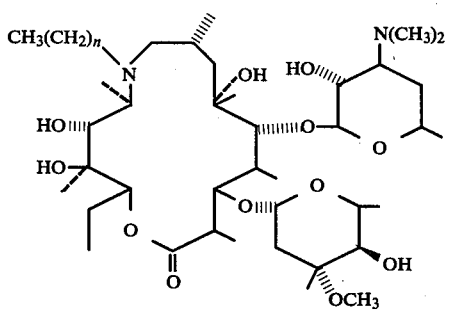

wherein n=1 or 2

Thus, for any given value of n, the epimeric forms of said compound differ structurally only in the configuration of the chiral center at the 4''-position; i.e., the 4'''—OH group is either axial or equatorial. The axial configuration is represented by a solid or wedged shape line and the equatorial by a broken line of attachment of the OH group to the 4''-position.

Acid addition salts of the compounds of this invention are readily prepared by treating compounds having formula (I) with at least an equimolar amount of the appropriate acid in a reaction-inert solvent or, in the case of the hydrochloride salts, with pyridinium hydrochloride. Since more than one basic group is present in a compound of formula (I), the addition of sufficient acid to satisfy each basic group permits formation of polyacid addition salts. The acid addition salts are recovered by filtration if they are insoluble in the reaction-inert solvent, by precipitation by addition of a nonsolvent for the acid addition salt, or by evaporation of the solvent.

A variety of Gram-positive microorganisms and certain Gram-negative microorganisms, such as those of spherical or ellipsoidal shape (cocci), are susceptible to compounds of formula (I). Their in vitro activity is readily demonstrated by in vitro tests against various microorganisms in a brain-heart infusion medium by the usual two-fold serial dilution technique. Their in vitro activity renders them useful for topical application in the form of ointments, creams and the like, for sterilization purposes, e.g. sick room utensils; and as industrial antimicrobials, for example, in water treatment, slime control, paint and wood preservation.

For in vitro use, e.g. for topical application, it will often be convenient to compound the selected product by methods well known in the pharmacist's art into lotions, salves, ointments, creams, gels or the like. For such purposes, it will generally be acceptable to employ concentrations of active ingredients of from about 0.01 percent up to about 10 percent by weight based on total composition. The dosage form is applied at the site of infection ad libitum, generally at least once a day.

Additionally, formula (I) compounds of this invention are active versus Gram-positive and certain Gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for 4 days after the last treatment and the number of survivors is noted.

When used in vivo, these novel compounds can be administered orally or parenterally, e.g. by subcutaneous or intramuscular injection, at a dosage of from about 1 mg/kg. to about 200 mg/kg. of body weight per day. The favored dosage range is from about 5 mg/kg. to about 100 mg/kg. of body weight per day and the preferred range from about 5 mg/kg. to about 50 mg/kg. of body weight per day. Vehicles suitable for parenteral injection may be either aqueous such as water, isotonic saline, isotonic dextrose, Ringer's solution or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

In the examples presented herein, no effort was made to recover the maximum amount of product produced or to optimize the yield of a given product. The Examples are merely illustrative of the process and of the products obtainable thereby.

In all examples, the terms "vanillin/ethanol/$H_3PO_4$ spray" and "vanillin/$H_3PO_4$ spray" refer to a solution of 1.0 g. of vanillin, 100 ml. of ethanol and 100 ml. of $H_3PO_4$.

The term "xylene" refers to the commercial mixture of xylene isomers, boiling range 137°–144° C.

EXAMPLE 1

9-Deoxo-9a-ethyl-9a-aza-9a-homoerythromycin A

To 10 ml. of methanol was added 1.0 g. (1.36 mmoles) of 9-deoxo-9a-aza-9a-homoerythromycin A (U.S. Pat. No. 4,328,334) and 5.95 g. (0.135 mole) of acetaldehyde, and the pH of the resulting solution adjusted to 5.95 with a 10% methanolic solution of acetic acid. To the reaction mixture was added 427 mg. (6.8 mmoles) of sodium cyanoborohydride portionwise over a period of ten minutes. After a final adjustment of the pH from 6.3 to 5.9 with methanolic acetic acid, the reaction mixture was allowed to stir at ambient temperature for eighteen hours. Methylene chloride (25 ml.) and water (25 ml.) were added, and the pH of the well-stirred mixture was maintained at 2.4 with 1N hydrochloric acid for twenty minutes. The organic layer was separated, combined with 25 ml. of fresh water and the pH adjusted to 2.4 with 1N hydrochloric acid. After stirring for twenty minutes the two aqueous phases from the pH 2.4 treatments were combined, treated with fresh methylene chloride and the pH of the mixture adjusted to 9.5 with 3N aqueous sodium hydroxide. The organic phase was separated and the aqueous layer extracted with fresh (2×50 ml.) methylene chloride. The organic extracts (3) were combined, dried over sodium sulfate and concentrated in vacuo to give 650 mg. of the crude product as a foam.

A 550 mg. sample of the crude product was chromatographed on 70–230 mesh silica gel using chloroform, methanol, concentrated ammonium hydroxide (9:1:0.1, v,v,v) as the eluent. Fractions comprised of 10 ml. each were collected and monitored by thin-layer chromatography using silica gel plates and methylene chloride, methanol, concentrated ammonium hydroxide (6:1:0.1, v,v,v) as the mobile phase and ethanolic vanillin-phosphoric acid spray with heat as the detection reagent. The fractions containing the product were combined and concentrated under vacuum to dryness to give 82 mg. of the pure product.

Mass Spectrum: m/e 762.5 (M+), 604.4, 587.4, 446.3, 170.2 and 158.2.

EXAMPLE 2

9-Deoxo-9a-ethyl-9a-aza-9a-homoerythromycin A

A solution of 15 g. (20 mmoles) 9-deoxo-9a-aza-9a-homoerythromycin A (U.S. Pat. No. 4,328,334) and 30.5 ml. of 37% aqueous acetaldehyde (0.2 mole) in 150 ml. of ethanol was combined with 15 g. of 5% palladium-on-charcoal (50% water wet) and shaken in a hydrogen atmosphere at an initial pressure of 50 psi for sixteen hours. The catalyst was filtered and the filtrate concentrated to dryness in vacuo. The colorless residue was treated with 200 ml. of methylene chloride and 200 ml. of water, and the pH of the well stirred mixture adjusted to 7.5. The organic phase was separated, washed with water and dried over sodium sulfate. Removal of the solvent gave 12.7 g. of the crude product as a foam. The crude product was chromatographed on 70–230 mesh silica gel using methylene chloride, methanol, concentrated ammonium hydroxide (9:1:0.05, v,v,v) as the eluent. Fractions comprised of 100 ml. each were collected and monitored by thin-layer chromatography using silica gel plates and chloroform, methanol, concentrated ammonium hydroxide (6:1:0.1, v,v,v) as the mobile phase. The fractions containing the product were combined and concentrated to dryness in vacuo to give 2.7 g. of the pure product as a colorless foam. The product was identical in every respect with that prepared in Example 1.

Mass Spectrum: m/e 762.5 (M+), 604.4, 587.4, 446.3, 170.2 and 158.2.

EXAMPLE 3

9-Deoxo-9a-(n-propyl)-9a-aza-9a-homoerythromycin A

A.

9-deoxo-9a-(beta-cyanoethyl)-9a-aza-9a-homoerythromycin A

9-Deoxo-9a-aza-9a-homoerythromycin A (1.0 g) was dissolved in 10.0 ml of acrylonitrile. The mixture was refluxed for 6 hours; then stirred overnight at ambient temperature. The mixture was then concentrated in vacuo to a tan foam. Chromatography of the crude product on silica gel (40 g; 70–230 mesh), eluting with a $CH_2Cl_2/CH_3OH$/concentrated $NH_4OH = 10/1/0.01$ solvent mixture and monitoring fractions by tlc (silica gel plates; $CH_2Cl_2/CH_3OH$/concentrated $NH_4OH = 6/1/0.1$ eluting system; vanillin/$H_3PO_4$ spray indicator with heat; Rf=0.57), afforded 605 mg. (56% yield) of the title compound as a colorless foam.

$^1$H-nmr (CDCl$_3$) delta 2.34 [6H, s, (CH$_3$)$_2$N—], 3.33 (3H, s, cladinose CH$_3$O—); $^{13}$C-nmr [CDCl$_3$, (CH$_3$)$_4$Si internal standard] ppm 177.62 (lactone>C=O), 118.85 (—C≡N), 103.01 (C-1'), 95.91 (C-1"), 40.33 [(CH$_3$)$_2$N—].

B.

9-deoxo-9a-(gamma-aminopropyl)-9a-aza-9a-homoerythromycin A

A solution of 47 g (59.6 mmole) of 9-deoxo-9a-(beta-cyanoethyl)-9a-aza-9a-homoerythromycin A in 520 ml. of ethanol was combined with 47 g. of Raney-Ni catalyst (50% water-wet) and hydrogenated on a Parr apparatus at 50 psi for 2.75 hours. Tlc inspection (silica gel plates; elution with CHCl$_3$/CH$_3$OH/concentrated NH$_4$OH=6/1/0.01; vanillin/H$_3$PO$_4$ spray with heat) showed the reaction to be incomplete. The mixture was charged with 25 g. of fresh catalyst, and hydrogenation at 50 psi (3.52 kg/cm$^2$) was continued for an additional 1.25 hours. The catalyst was filtered and the filtrate was concentrated in vacuo to a colorless foam. The crude product was dissolved in 600 ml of ethyl acetate. The solution was stirred with 800 ml of water and the pH was adjusted to 9.5 with 6N sodium hydroxide. The organic phase was dried over sodium sulfate and concentrated in vacuo to a foam. Chromatography on silica gel (800 g, 70–230 mesh) eluting with CHCl$_3$/CH$_3$OH/concentrated NH$_4$OH=6/1/0.05; Rf=0.15, afforded 14.7 g (31% yield) of the pure title compound as a colorless foam.

Crystallization of a 1.1 g. sample from diethyl ether gave 545 mg. of colorless crystals; m.p. 180°–183° C.

$^1$H-nmr (CDCl$_3$) delta 2.30 [6H, s, (CH$_3$)$_2$N—], 3.32 (3H, s, cladinose CH$_3$O); $^{13}$C-nmr [CDCl$_3$, (CH$_3$)$_4$Si internal standard] ppm 177.01 (lactone>C=O), 102.69 (C-1'), 95.27 (C-1"), 40.33 [(CH$_3$)$_2$N—].

C.

9-deoxo-9a-(gamma-formamidopropyl)-9a-aza-9a-homoerythromycin A

To a stirred solution of 3.0 g. (3.8 mmoles) of 9-deoxo-9a-(gamma-aminopropyl)-9a-aza-9a-homoerythromycin A in 25 ml. of methylene chloride at 5° C. was added 370 mg. (4.2 mmoles) of acetic-formic anhydride in 5 ml. of methylene chloride dropwise over a period of 5 minutes. The ice bath was removed after the addition was complete, and the reaction mixture stirred at 25° C. for one hour. The reaction was shaken with an equal volume of a 10% aqueous potassium carbonate solution.

The organic phase was separated, washed with a saturated brine solution and dried over sodium sulfate. Removal of the solvent in vacuo gave 3.1 g. of the product as a colorless foam.

¹H-nmr (CDCl₃) delta 2.25 [6H, s, (CH₃)₂N—), 3.28 (3H, s, cladinose CH₃O—), 6.77 (1H, broad, —CONH—) and 8.15 (1H, broad,

¹³C-nmr [CDCl₃, (CH₃)₄Si internal standard) ppm 177.77 (lactone>C=O), 161.89

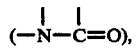

103.01 (C-1'), 95.78 (C-1") and 40.30 [(CH₃)₂N—].

D.
9-deoxo-9a-(gamma-isonitrilopropyl)-9a-aza-9a-homoerythromycin A

To a stirred solution of 4.6 g. (5.6 mmoles) of 9-deoxo-9a-(gamma-formamidopropyl)-9a-aza-9a-homoerythromycin A in 30 ml. of pyridine at 5° C. was added a solution of 2.7 g. (14 mmoles) of p-toluene-sulfonyl chloride in 10 ml. of pyridine dropwise over a period of ten minutes. The cooling bath was removed and the reaction mixture was stirred at room temperature for seventy-five minutes. The reaction mixture was concentrated to dryness under vacuum and the residue taken up in 150 ml. of methylene chloride and 150 ml. of water. The pH of the well stirred mixture was then adjusted to 10 with a 10% aqueous potassium carbonate solution. The organic layer was separated, washed with water (2×100 ml.) and then washed with a brine solution (1×100 ml.). After drying over anhydrous potassium carbonate the organic layer was concentrated to dryness in vacuo to give 5 g. of the desired product as an amber foam.

The infra-red spectrum (CCl₄) showed absorption at 1725 (lactone>C=O) and

E. 9-deoxo-9a-(n-propyl)-9a-aza-9a-homoerythromycin A

To a well stirred solution of 5 g. (6.25 mmoles) of 9-deoxo-9a-(gamma-isonitrilopropyl)-9a-aza-9a-homoerythromycin A and 91 g. (0.312 mole) of tri-n-butyl tin hydride in 50 ml. of xylene at 125° C. was added dropwise over a period of one hour 5.12 g. (31.2 mmoles) of azobisisobutylnitrile suspended in 50 ml. of xylene. On completion of the addition, the reaction mixture was maintained at 125° C. for forty-five minutes, and was then allowed to cool. Ethyl acetate (75 ml.) and 75 ml. of water were added to the reaction and the pH of the well stirred mixture adjusted to 4.5 with 6N hydrochloric acid. After stirring for twenty minutes the phases were separated and the organic phase stirred with 50 ml. of fresh water at pH 4.5. The two aqueous extracts were combined and washed with fresh ethyl acetate (2×30 ml.). The aqueous layer was separated, combined with 50 ml. of fresh ethyl acetate and the pH of the resulting mixture adjusted to 10 with a 10% aqueous potassium carbonate solution. The organic phase was separated, washed with water (50 ml.) and a brine solution (50 ml.) and dried over anhydrous potassium carbonate. Removal of the solvent under vacuum gave 3.9 g. of the crude product as an amber foam.

A sample of 3.1 g. of the crude product was chromatographed on 285 g. of 230-400 mesh silica gel using initially 1 l. of chloroform, methanol, concentrated ammonium hydroxide (96:3.2:0.3, v,v,v) as the eluent followed by chloroform, methanol, concentrated ammonium hydroxide (92:7.2:0.72, v,v,v). The fractions were monitored by thin layer chromatography using the same solvent combination as the mobile phase on silica gel plates. The fractions containing the product were combined and concentrated in vacuo to give 391 mg. of the desired product as a colorless foam.

¹³C-nmr (CDCl₃) ppm 178.0 (lactone>C=O), 103.28 (C-1'), 95.47 (C-1"), 84.03 (C-5), 40.43 [(CH₃)₂N—]; Mass Spectrum: m/e 460.33, 444.33, 429.34, 402.29, 184,158 and 127.

I claim:
1. A compound having the formula

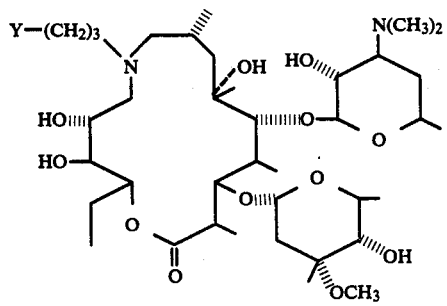

wherein Y is —NHCHO or

2. The compound of claim 1, wherein Y is —NHCHO.

3. The compound of claim 1, wherein Y is

4. A process for making a compound of the formula

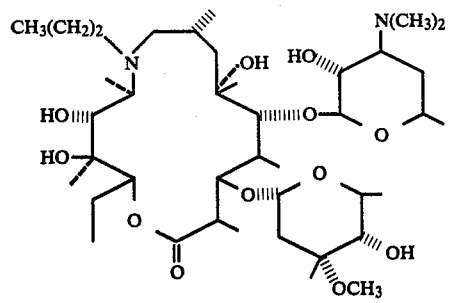

which comprises reacting a compound of the formula

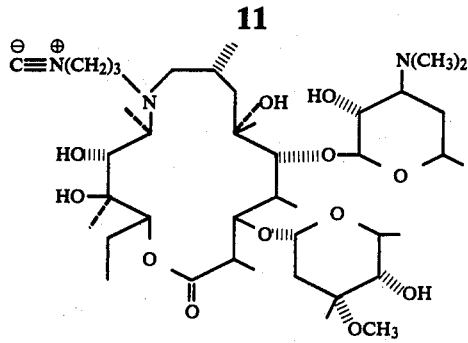
with tri-n-butyl tin hydride and azobisiosbutylnitrile in a reaction inert solvent at a reaction temperature of about 125° C.
5. The process of claim 4, wherein the solvent is xylene.
* * * * *